(12) United States Patent
Fahey

(10) Patent No.: US 6,737,441 B2
(45) Date of Patent: May 18, 2004

(54) TREATMENT OF HELICOBACTER WITH ISOTHIOCYANATES

(75) Inventor: Jed W. Fahey, 406 WBSB 725 N. Wolfe St., Baltimore, MD (US) 21205-2185

(73) Assignee: Jed W. Fahey, Eldersburg, MD (US)

( * ) Notice: Subject to any disclaimer, the term of this patent is extended or adjusted under 35 U.S.C. 154(b) by 0 days.

(21) Appl. No.: 09/933,170

(22) Filed: Aug. 21, 2001

(65) Prior Publication Data

US 2002/0151505 A1 Oct. 17, 2002

Related U.S. Application Data

(60) Provisional application No. 60/226,520, filed on Aug. 21, 2000.

(51) Int. Cl.[7] ........................ A61K 31/27; A61K 35/78; A01N 47/40
(52) U.S. Cl. ........................ 514/514; 514/515; 514/24; 424/755
(58) Field of Search ................................ 514/514, 515, 514/24; 424/755

(56) References Cited

U.S. PATENT DOCUMENTS

| | | | | |
|---|---|---|---|---|
| 5,114,969 A | * | 5/1992 | Chung et al. ................ | 514/514 |
| 5,589,504 A | * | 12/1996 | Dannenberg et al. ....... | 514/456 |
| 5,725,895 A | * | 3/1998 | Fahey et al. ................ | 426/49 |
| 5,968,505 A | * | 10/1999 | Fahey et al. ................ | 424/94.1 |
| 5,968,567 A | * | 10/1999 | Fahey et al. ................ | 426/49 |
| RE36,784 E | | 7/2000 | Cho et al. | |
| 6,177,122 B1 | * | 1/2001 | Fahey et al. ................ | 426/629 |
| 6,340,784 B1 | * | 1/2002 | Mithen et al. ............... | 800/36 |
| 6,348,220 B1 | * | 2/2002 | Ribnicky et al. ........... | 424/725 |
| 6,465,512 B2 | * | 10/2002 | Nakamura et al. ......... | 514/514 |

FOREIGN PATENT DOCUMENTS

WO  WO 97/26908 A1  7/1997

OTHER PUBLICATIONS

Database WPI, Section Ch, Week 198632 Derwent Publications Ltd., London, GB; AN 1986-209527; XP002198443 & JP 61 143353 A (Denki Kagaku Kogyo KK), Jul. 1, 1986 abstract only.

Zhang et al., :Anticarcinogenic activities of organic isothiocyanates: chemistry and mechanisms. Database Medline 'Online! Apr. 1, 1994; database accsssion No. NLM8137323, XP002198442 abstract & Cancer Research, vol. 54, No. 7 Suppl., Apr. 1, 1994 pages 1976s–1981s, ISSN: 0008-5472.

Fahey et al., "Antioxidant Functions of Sulforaphane: a Potent Inducer of Phase II Detoxication Enzymes," *Food and Chemical Toxicology*: 37:973–979 (1999) ISSN: 0278-6915.

Alain Lozniewski, et al. "Human Embryonic Gastric Xenografts in Nude Mice: a New Model of *Helicobacterpylori*Infection," *Infection And Immunity*(Apr. 1999) 67(4): 1798–1805, American Society for Microbiology.

Haim Shirin et al., "*Helicobacter pylori*decreases gastric mucosal glutathione," *Cancer Letters*.(Mar. 2001) 164: 127–133 Elsevier Science Ireland Ltd.

Yuesheng Zhang et al., "A major inducer of anticarcinogenic protective enzymes from broccoli: Isolation and elucidation of structure," *Proc. Natl. Acad. Sci.*(Mar. 1992) 89:2399–2403 (Mar., 1992).

G. Roger Fenwick et al., "Glucosinolates and Their Breakdown Products in Food and Food Plants," *CRC Crit. Rev. Food Sci. Nutr.*(1983) 18:123–201, CRC Press.

Jan Jorn Hansen et al., "Intramolecular Cycilzations of Thioureas Derived from Sulphoraphene: A Case of Asymmetrically Induced Additions to Vinylic Sulphoxides," *Acta Chemica Scandinavica B*.(1974) 28(4):418–424 Chemical Societies in Denmark, Finland, Norway and Sweden.

Kurt Mislow et al., "Optical Rotatory Dispersion an Absolute Configuration of Dialkyl Sulfides," *Journal of the American Chemical Society*.(Feb. 1965) 87(3): 665–666.

Jed W. Fahey et al., "The cheical diversity and distributin of glucosinolates and isothiocyanates among plants," *Phytochemistry*(Jan. 2001) 56:5–51 Elsevier Science Ltd.

* cited by examiner

Primary Examiner—Zohreh Fay
Assistant Examiner—Brian-Yong S. Kwon
(74) Attorney, Agent, or Firm—Foley & Lardner

(57) ABSTRACT

The present invention relates to methods of preventing or inhibiting the growth of Helicobacter through the use of a composition that comprises a glucosinolate, an isothiocyanate or a derivative or metabolite thereof. The present invention also relates to methods of preventing or treating persistent chronic gastritis, ulcers and/or stomach cancer in subjects at risk for, or in need of treatment thereof.

51 Claims, No Drawings

TREATMENT OF HELICOBACTER WITH ISOTHIOCYANATES

This application claims priority to U.S. Provisional Application Serial No. 60/226,520, filed Aug. 21, 2000.

STATEMENT REGARDING FEDERALLY SPONSORED RESEARCH OR DEVELOPMENT

Part of the work performed during development of this invention utilized U.S. Government funds. The U.S. Government has certain rights in this invention.

BACKGROUND OF THE INVENTION

1. Field of the Invention

The present invention relates to methods of preventing or inhibiting the growth of Helicobacter through the use of a composition that comprises a glucosinolate, an isothiocyanate or a derivative or metabolite thereof. The present invention also relates to methods of preventing or treating persistent chronic gastritis, ulcers and/or stomach cancer in subjects at risk for, or in need of treatment thereof.

2. Background of the Invention

Stomach cancer is the second most common form of cancer worldwide. *Helicobacter pylori* is a microaerophilic, gram-negative bacterium of cosmopolitan distribution that causes persistent chronic gastritis. Carriers of *H. pylori* (in gastric mucosa) are at 3 to 6 times the risk for developing stomach cancer (gastric adenocarcinoma and mucosa-associated lymphoid tissue lymphoma) as non-carriers (J. Danesh et al., *Cancer Surveys*, 33:263–289 (1999); D. Forman et al., *Br Med Bull*, 54:71–78 (1998); S. Hansen et al., *Scand J Gastroenterol*, 34:353–360 (1999); J-Q Huang et al., *Gastroenterology*, 114:1169–1179(1998)). *H. pylori* causes inflammation of stomach tissue in carriers, resulting in increased blood flow, swelling and irritation. Inflammation of the lower part of the stomach leads to ulcers in about 10% of carriers. Inflammation of the upper part of the stomach leads to impaired acid secretion and ultimate die-off of acid-producing cells and leads to reduced stomach function and ultimately to cancer.

*Helicobacter pylori* was only first described following its cultivation from human gastric biopsy specimens in 1982 (J R Warren et al., Lancet, (1983), 1:1273–1275; B J Marshall et al., Microbios Lett. (1984), 25:83–88). Since then, as many as 26 related Helicobacter species have been described colonizing the mucosal surfaces of humans and other animals (J V Solnick, D B Schauer, Clin Microbiol Rev, (2001), 14:59–97). These organisms not only colonize gastric tissues of mammals, but are found in the intestinal tract and the liver of birds, as well as in mammals including humans, mice, ferrets, gerbils, dogs and cats. They have been implicated as agents responsible for inflammation, and in malignant transformation in immunocompetent hosts as well as immunocompromised humans and animals. However, *H. pylori* is now well-documented as one of the most prevalent human pathogens worldwide (R M Genta et al., *Virchows Arch*, 425:339–347 (1994)), and the causal agent for most gastric and duodenal ulcers, as well as a risk factor for the development of gastric cancer (J Danesh, *Cancer Surveys*, 33:263–289 (1999)). The human stomach is the only known natural reservoir for *H. pylori*, although many mammalian species can be infected by related species. Antibiotic therapy aimed at eradication of *H. pylori* (e.g. amoxycillin and clarithromycin plus the $H_2$ inhibitor omeprazol for 10–14 days) is now recommended for infected patients who have verified peptic ulcerations of the stomach or duodenum or who have gastric mucosa-associated lymphoid tissue lymphomas, and cure rates are on the order of 90% (Helicobacter Foundation, "Treatment of *Helicobacter pylori*, p. 1–5 (1998)). However, a complex antibiotic therapy as described above may not be available in developing countries, where *H. pylori* infection rates can be as high as 70% of the population.

Thus a need exists for an economical dietary supplement, food or pharmaceutical that will naturally inhibit the growth and/or infection rates of *H. pylori*, both in the lumen of the stomach and within gastric epithelial cells where *H. pylori* may serve as a low-level, chronic reservoir for re-infection. This inhibition of eradication can in turn reduce the incidence of ulcers and stomach cancer or prevent reinfection of *H. pylori*.

SUMMARY OF THE INVENTION

The present invention relates to a method of treating a subject having a Helicobacter infection, comprising administering to the subject an antibacterially effective amount of a composition that comprises a glucosinolate, an isothiocyanate or a derivative thereof.

The present invention also relates to a method of preventing a Helicobacter infection in a subject, comprising treating the subject with an antibacterially effective amount of a composition that comprises a glucosinolate, an isothiocyanate or a derivative thereof.

The present invention further relates to a method for inhibiting the growth of Helicobacter, comprising administering an antibacterially effective amount of an agent selected from the group consisting of a glucosinolate, an isothiocyanate or a derivative thereof.

BRIEF DESCRIPTION OF THE DRAWINGS

N/A

DETAILED DESCRIPTION OF THE PREFERRED EMBODIMENTS

The present invention relates to a method of treating a subject having a Helicobacter infection, comprising administering to the subject an antibacterially effective amount of a composition that comprises a glucosinolate, an isothiocyanate or a derivative thereof.

Helicobacter is a gram-negative bacterium with polar flagella, using oxygen as an electron acceptor, which cannot utilize carbohydrates as an energy source. The Helicobacter genus is fully characterized in Versalovic, et al, *Manual of Clinical Microbiology*, 7th Ed., pp. 727–738 (1999) and Perez-Perez, et al., *Medical Microbiology*, 4th Ed., pp. 311–322 (1996), which are incorporated herein by reference. Helicobacter is used interchangeably with "Helicobacter sp" herein.

As used herein, the terms subject or patient are used interchangeably and are used to mean any animal, preferably a mammal, including humans and non-human primates. In one embodiment of the current invention the subject having a Helicobacter infection is suffering from a peptic ulcer. Peptic ulcers, as contemplated in the current invention include, but are not limited to, circumscribed breaks in the continuity of the mucosal layer of the gastrointestinal tract. These breaks in the continuity of the mucosal layer can include breaks that extend below the epithelium, or breaks that do not extend below the epithelium, sometime referred to as "erosions." The peptic ulcers may be acute, or chronic. Further, peptic ulcers can be located in any part of the gastrointestinal tract that is exposed to acid-pepsin gastric juice, including the esophagus, stomach, duodenum, and after gastroenterostomy, the jejunum.

In another embodiment of the current invention the subject having the Helicobacter infection is suffering from, or at risk of developing, cancer of the gastrointestinal tract. As stated previously, the portions of the gastrointestinal tract where cancer may be present are any areas where the tract is exposed to acid-pepsin gastric juice, including the esophagus, stomach, duodenum, and after gastroenterostomy, the jejunum. As used herein the term cancer is used as one of ordinary skill in the art would recognize the term. Examples of cancers include, but are not limited to, neoplasias (or neoplasms), hyperplasias, dysplasias, metaplasias, hypertrophies. The neoplasms may be benign or malignant, and they may originate from any cell type, including but not limited to epithelial cells of various origin, muscle cells and endothelial cells.

The treatment envisioned by the current invention can be used for patients with a pre-existing Helicobacter infection, or for patients pre-disposed to a Helicobacter infection. Additionally, the method of the current invention can be used to correct or compensate for cellular or physiological abnormalities involved in conferring susceptibility to Helicobacter infection in patients, and/or to alleviate symptoms of a Helicobacter infection in patients, or as a preventative measure in patients.

As used herein, the phrase Helicobacter infection is used to mean an interaction between Helicobacter and the host organism (subject). The infections may be localized, meaning that the Helicobacter grows and remains near the point of initial interaction. The infection may also be generalized, where the Helicobacter may become more widespread beyond the initial point of interaction, including spreading to the surrounding tissue or organ and even being distributed and growing throughout the entire host organism. As used herein, the term interaction (of a host and microorganism) is used to mean a process where the Helicobacter grows in or around a particular tissue. To illustrate, the Helicobacter is considered to have infected the subject if the bacteria is able to penetrate the surface of cells of a particular tissue and grow within the cells of the tissue. An example of this type of infection includes, but is not limited to Helicobacter penetrating and growing within the epithelial cells lining the lumen of the stomach. Additionally, the Helicobacter can also be said to have infected the host organism by growing extracellularly to the tissue cells.

The method of the current invention comprises administering an antibacterially effective amount of a composition to treat a Helicobacter infection. As used herein, "an antibacterially effective amount" is intended to mean an amount effective to prevent, inhibit, retard or reverse the growth of Helicobacter, and/or to reduce the number of viable Helicobacter cells within the stomach or at a site of infection without excessive levels of side effects. "Antibacterially effective amount" is also used to mean an amount effective to kill, reduce or ameliorate any existing infections of Helicobacter where the infection takes place prior to the administration of the compositions used in the current invention. Thus as the current invention contemplates, an antibacterially effective amount of the compositions of the current invention can be used as a treatment to a pre-existing Helicobacter infection. Effective amounts for use in these treatments can completely or partially prevent a pre-existing infection from spreading to surrounding tissue and beyond, and they can also be used to slow the growth and/or spread rate of the Helicobacter in the subject. Furthermore, the antibacterially effective amounts of the compositions used in the current invention can prevent a Helicobacter infection in subjects. Another aspect of "antibacterially effective amount," as used in the current invention, means that the compositions administered to the subject are capable of preventing or reducing the cellular or physiological damage to the infected or surrounding tissue, caused by the toxins produced by the Helicobacter. In still another aspect, the phrase antibacterially effective amount can be used to mean an amount of the administered composition that can reduce or prevent the formation or efficacy of the virulence of the Helicobacter. By virulence is meant the ability of the Helicobacter to combat the host organism's or cell's natural defenses to the Helicobacter infection.

The method of treating a subject having a Helicobacter infection involves administration of compositions to the subjects. As used herein, composition can mean a pure compound, agent or substance or a mixture of two or more compounds, agents or substances. As used herein, the term agent, substance or compound is intended to mean a protein, nucleic acid, carbohydrate, lipid, polymer or a small molecule, such as a drug.

The compositions for use in the current invention comprise isothiocyanates, glucosinolates or derivatives or metabolites thereof such as, but not limited to: nitriles, carbamates, thiocarbamates, thiocyanates. As used herein derivatives include metabolites and/or analogs of isothiocyanates or glucosinolates. The term derivatives is used herein to encompass derivatives, analogs and metabolites of isothiocyanates or glucosinolates. Additionally, the compositions of the current invention also include combinations of different isothiocyanates, glucosinolates or derivatives thereof or their combination with other therapeutic moieties or agents. Isothiocyanates are compounds containing the isothiocyanate (—NCS$^-$) moiety and are easily identifiable by one of ordinary skill in the art. An example of an isothiocyanate includes, but is not limited to sulforaphane or its analogs. The description and preparation of isothiocyanate analogs is described in U.S. Reissue Pat. No. 36,784, and is hereby incorporated by reference in its entirety. In a preferred embodiment, the sulforaphane analogs used in the present invention include 6-isothiocyanato-2-hexanone, exo-2-acetyl-6-isothiocyanatonorbornane, exo-2-isothiocyanato-6-methylsulfonyinorbornane, 6-isothiocyanato-2-hexanol, 1-isothiocyanato-4-dimethylphosphonylbutane, exo-2-(1'-hydroxyethyl)-5-isothiocyanatonorbornane, exo-2-acetyl-5-isothiocyanatonorbornane, 1-isothiocyanato-5-methylsulfonylpentane, cis-3-(methylsulfonyl)cyclohexylmethylisothiocyanate and trans-3-(methylsulfonyl)cyclohexylmethylisothiocyanate. Other isothiocyanates also include, but are not limited to, conjugates of isothiocyanates, which include, among others, glutathione-, cysteinylglycine-, cysteinyl-, and N-acetylcysteine-conjugates.

Glucosinolates, which are well-known in the art, are precursors to isothiocyanates. Examples of glucosinolates include, but are not limited to, glucoraphanin, glucoerysolin, glucoerucin, glucoiberin, glucoalyssin, glucoberteroin, glucoiberverin, glucocheirolin, glucoraphenin, 5-methylsulfinylpentyl glucosinolate, 6-methylsulfinylhexyl glucosinolate, 7-methylsulfinylheptyl glucosinolate, 8-methylsulfinyloctyl glucosinolate, 9-methylsulfinylnonyl glucosinolate, 10-methylsulfinyldecyl glucosinolate, phenylethyl glucosinolate, 4-(α-L-rhamnopyranosyloxy)benzyl glucosinolate, 3-(α-L-rhamnopyranosyloxy)benzyl glucosinolate, 2-(α-L-rhamnopyranosyloxy)benzyl glucosinolate, 4-(4'-O-acetyl-α-L-rhamnopyranosyloxy) benzyl glucosinolate as well as those reviewed in Table 1 of Fahey et al., Phytochemistry, 56:5–51 (2001) and corrigenda thereto, the entire contents of which are incorporated herein by reference, and the products of their myrosinase-catalyzed hydrolysis (e.g. their cognate isothiocyanates, thiocyanates, nitrites, carbamates and thiocarbamates). Glucosinolates are easily recognizable and appreciated by one of ordinary skill in the art and are reviewed in Fahey et al., Phytochemistry, 56:5–51 (2001) and corrigenda thereto, the entire contents of which are hereby incorporated by reference.

In one embodiment of the current invention, the isothiocyanate for use in the current invention is sulforaphane, or a derivative thereof. In a further embodiment, the isothiocyanate is sulforaphane.

Sulforaphane (4-methylsulfinylbutyl isothiocyanate or (−)-1-isothiocyanato-4(R)-(methylsulfinyl) butane) and sulforaphene (4-methylsulfinylbutenyl isothiocyanate) and their cognate glucosinolates (glucoraphanin and glucoraphenin, respectively), are known to be produced by plants, such as hoary cress, radish and other plants (Mislow et al., *J. Am. Chem. Soc.*, 87:665–666 (1965); Schmid et al., *Helvet. Chim. Acta*, 31:1017–1028 (1942); Hansen et al., *Acta Chem. Scand. Ser., B* 28:418–424 (1974)). For the purposes of the present invention, they can be isolated from plants or synthesized. Bertoin, alyssin, erucin, erysolin, iberverin, iberin, and cheirolin can also be isolated from plants; these compounds appear to be less active as inducers than sulforaphane and sulforaphene, at least in cell culture.

Other synthetic analogues include compounds with sulfur-containing-, olefinic, aliphatic, and multiply glycosylated-side chains.

Other analogues of sulforaphane can be used which are not specifically shown. The relative ability of the compound to inhibit or prevent the growth of Helicobacter, or treat subjects with Helicobacter infections can be assessed as taught below, either by testing inhibition in cell lines, or in whole animals.

Provided by the present invention are food products which have been supplemented with a composition or agent of the present invention. The compositions or agents used as food supplements should contain isothiocyanates, glucosinolates or derivatives thereof. The supplement may be isolated from plants or synthesized. Also provided by the present invention are foods and/or plants that contain high levels of glucosinolates or isothiocyanates. Examples of plants that contain glucosinolates or isothiocyanates include, but are not limited to, Brassicaceae (Cruciferae), Moringaceae and Resedaceae, which collectively include, but are not limited to, broccoli, broccoli sprouts, Brussels sprouts, cabbage, cauliflower, cauliflower sprouts, daikon, horseradish, kale, mustard seed, radish, wasabi, horseradish tree (*Moringa oleifera*), cabbage tree (*M. stenopetala*), mignonette (*Reseda odorata*), dyer's rocket (*R. luteola*). Other families of plants that contain glucosinolates include, but are not limited to, Bataceae, Bretschneideraceae, Capparaceae, Caricaceae, Euphorbiaceae, Gyrostemonaceae, Limnanthaceae, Pentadiplandraceae, Phytolaccaceae, Pittosporaceae, Salvadoraceae, Tovariaceae and Tropaeolaceae. These high levels may occur naturally or plants may be bred to contain high levels or glucosinolates or isothiocyanates.

Glucosinolates and/or isothiocyanates can be purified from seed or plant extracts by methods well known in the art. (See Fenwick et al., *CRC Crit. Rev. Food Sci. Nutr.* 18: 123–201 (1983) and Zhang et al., *Proc. Natl Acad. Sci. USA* 89: 2399–2403 (1992)). Purified or partially purified glucosinolate(s) or isothiocyanate(s) can be added to food products as a supplement. The dose of glucosinolate and/or isothiocyanate added to the food product preferably is in the range of 1 μmol to 1,000 μmol per serving. However, the dose of glucosinolate and/or isothiocyanate supplementing the food product can be higher.

The selection of plants having high levels of glucosinolates or isothiocyanates in sprouts, seeds or other plant parts can be incorporated into Brassica (Crucifer) breeding programs. In addition, these same breeding programs can include the identification and selection of cultivars that have high levels of glucosinolates or isothiocyanates. Strategies for the crossing, selection and breeding of new cultivars of Brassicaceae (Cruciferae) are well known to the skilled artisan in this field. (*Brassica Crops and Wild Allies: Biology & Breeding*; S. Tsunoda et al. (eds), Japan Scientific Societies Press, Tokyo pp. 354 (1980); *Biology of Brassica Coenospecies*; C. Gomez-Campo (ed), Elsevier, Amsterdam p. 489 (1999)). Progeny plants are screened for high levels of glucosinolates or isothiocyanates produced at specific plant developmental stages. Plants carrying the trait of interest are identified and the characteristic intensified or combined with other important agronomic characteristics using breeding techniques well known in the art of plant breeding.

In one embodiment of the current invention, the composition used in the method of treating a Helicobacter infection can be in the form of a food, food supplement, a dietary supplement or food additive.

In one embodiment of the current invention, the composition administered to the subject is a pharmaceutical composition. Further, the pharmaceutical composition can be administered orally, nasally, parenterally, intrasystemically, intraperitoneally, topically (as by drops or transdermal patch), bucally, or as an oral or nasal spray. The term "parenteral," as used herein, refers to modes of administration which include intravenous, intramuscular, intraperitoneal, intrasternal, subcutaneous and intraarticular injection and infusion. The pharmaceutical compositions as contemplated by the current invention may also include a pharmaceutically acceptable carrier.

By "pharmaceutically acceptable carrier" is intended, but not limited to, a non-toxic solid, semisolid or liquid filler, diluent, encapsulating material or formulation auxiliary of any type.

A pharmaceutical composition of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention can also contain adjuvants such as, but not limited to, preservatives, wetting agents, emulsifying agents, and dispersing agents. Prevention of the action of microorganisms can be ensured by the inclusion of various antibacterial and antifungal agents, for example, paraben, chlorobutanol, phenol, sorbic acid, and the like. It can also be desirable to include isotonic agents such as sugars, sodium chloride, and the like. Prolonged absorption of the injectable pharmaceutical form can be brought about by the inclusion of agents which delay absorption such as aluminum monostearate and gelatin.

In some cases, to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar—agar, and tragacanth, and mixtures thereof.

Alternatively, the composition can be pressurized and contain a compressed gas, such as nitrogen or a liquefied gas propellant. The liquefied propellant medium and indeed the total composition is preferably such that the active ingredients do not dissolve therein to any substantial extent. The pressurized composition can also contain a surface active agent. The surface active agent can be a liquid or solid non-ionic surface active agent or can be a solid anionic surface active agent. It is preferred to use the solid anionic surface active agent in the form of a sodium salt.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 et seq (1976)).

One of ordinary skill will appreciate that effective amounts of the agents of the invention can be determined empirically and can be employed in pure form or, where such forms exist, in pharmaceutically acceptable salt, ester or prodrug form. The agents can be administered to a subject, in need of treatment of a Helicobacter infection, as pharmaceutical compositions in combination with one or more pharmaceutically acceptable excipients. It will be understood that, when administered to a human patient, the total daily usage of the agents or composition of the present invention will be decided by the attending physician within the scope of sound medical judgement. The specific therapeutically effective dose level for any particular patient will depend upon a variety of factors: the type and degree of the cellular or physiological response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

Dosing can also be arranged in a patient specific manner to provide a predetermined concentration of the agents in the blood, as determined by techniques accepted and routine in the art. Thus patient dosaging can be adjusted to achieve regular on-going blood levels, as measured by HPLC, on the order of from 50 to 1000 ng/ml.

It will be readily apparent to one of ordinary skill in the relevant arts that other suitable modifications and adaptations to the methods and applications described herein can be made without departing from the scope of the invention or any embodiment thereof.

In one embodiment of the current invention, the Helicobacter infection from which the subject is suffering is *Helicobacter pylori*.

In another embodiment, the methods of the current invention may further comprise administering an antibiotic, an antibiotic regimen or another drug to the subject or Helicobacter. The current pharmaceutical regimen for treating *H. pylori* includes antibiotic therapy. As used herein, the phrase "antibiotic" or "antibiotic therapy" is used as one of skill in the art would recognize such terms. Antibiotics for use in combination with the compositions or agents in the current invention include, but are not limited to, amoxycillin and clarithromycin. Other drugs that may be used in combination with the current invention include, but are not limited to, omeprazol.

The present invention also relates to a method of preventing a Helicobacter infection in a subject, comprising treating said subject with an antibacterially effective amount of a composition that comprises a glucosinolate, an isothiocyanate or a derivative thereof. Preferably, the method of preventing Helicobacter infection is performed on *Helicobacter pylori*.

As used herein the method of preventing a Helicobacter infection may be performed on subjects that have had previous infections, or on subjects with no history of Helicobacter infection.

In one embodiment of the current invention, the compositions used to prevent Helicobacter infection in a subject comprise sulforaphane or a derivative thereof. In a further embodiment, the composition is sulforaphane.

In another embodiment of the current invention, the composition used to prevent Helicobacter is a food, food supplement, dietary supplement or a food additive. In still another embodiment, the composition is a pharmaceutical composition. Preferably, the pharmaceutical composition is administered orally.

The current invention also relates to a method for inhibiting the growth of Helicobacter, comprising administering to said Helicobacter an antibacterially effective amount of an agent selected from the group consisting of a glucosinolate, a isothiocyanate or a derivative thereof. Preferably, the Helicobacter is *Helicobacter pylori*.

As used herein, inhibition of growth is used to mean growth under in vitro, in vivo or in situ conditions. Furthermore, inhibition of growth is used to mean the process where the bacteria cells stop or slow their rate of mitosis or normal metabolic processes. Inhibition of growth can also mean cell death. The various forms and signs of cell death are obvious to those skilled in the art, but examples of cell death include, but are not limited to, programmed cell death (i.e., apoptosis), gradual death of the cells as occurs in diseased states (i.e., necrosis), and more immediate cell death such as acute toxicity. The inhibition of growth of Helicobacter for which the current invention provides can be a complete or partial inhibition of growth or a complete or partial causation of cell death.

In one embodiment of the current invention, the compositions used to inhibit the growth of Helicobacter infection in a subject comprise sulforaphane or a derivative thereof. In a further embodiment, the composition is sulforaphane.

In another embodiment of the current invention, the composition used to inhibit the growth of Helicobacter is a food, food supplement, dietary supplement or a food additive. In still another embodiment, the composition is a pharmaceutical composition. Preferably, the pharmaceutical composition is administered orally.

In another embodiment, the compositions of the current invention may be combined with antibiotics or other drugs to prevent the growth of Helicobacter.

The current invention also relates to a method of identifying an agent that modulates the growth of Helicobacter comprising treating Helicobacter with said agent and assaying for growth of said Helicobacter; treating said Helicobacter with a known modulator of Helicobacter growth and assaying for growth of said Helicobacter, wherein said known modulator of Helicobacter growth is selected from the group consisting of a glucosinolate, an isothiocyanate and a derivative thereof; and comparing the levels of Helicobacter growth in (a) and (b) to determine if said agent modulates said growth of Helicobacter. Preferably, the method of screening agents that modulate the growth of Helicobacter is used to screen agents that modulate the growth of *Helicobacter pylori*.

In one embodiment of the current invention, the method of identifying an agent that modulates the growth Helicobacter is performed on a single population of cells, and (b) is performed on the identical population after the agent in (a) is removed. In another embodiment of the invention, the method of identifying an agent that modulates the growth Helicobacter is performed on two nearly identical populations of cells, under the same conditions, where (a) is performed on one population and (b) is performed on another population, and (c) is a comparison of the levels of the growth Helicobacter between the two populations of cells. Preferably, the methods of identifying growth modulators of Helicobacter are performed on *Helicobacter pylori*.

In another embodiment, of the current invention, the method of identifying an agent that modulates the growth Helicobacter is performed on cells other than Helicobacter cells, that have been infected with the Helicobacter prior to the assay. The Helicobacter may be present inside these other cells or it may be present around, or near, the cells. Examples of situations where the Helicobacter may be present in or around the other cell types include, but are not limited to, co-culturing cells with Helicobacter, allowing the Helicobacter to infect the other cell types prior to performing the assay. The other cells can be prokaryotic or eukaryotic, but preferably eukaryotic, and even more preferably animal cells. The animal cells for use in the current invention can be any type of cell found in an animal, including, but not limited to, epithelial, neuronal, endothelial and muscle cells.

In an additional embodiment, the methods of identifying agents that modulate the growth of Helicobacter can be carried out on cells that are in culture, i.e. in vitro, or in cells occurring in situ or in vivo. The cells may be part of a tissue or a whole organ. As used herein, the term tissue is used to mean a tissue as one of ordinary skill in the art would understand it to mean. As envisioned in the current application, tissue is also used to mean individual or groups of cells, or cell cultures, of a bodily tissue or fluid (e.g. blood cells). Furthermore, the tissue may be within a subject, or biopsied or removed from a subject. The tissue may also be a whole or any portion of a bodily organ. Additionally, the tissue may be "fresh" in that the tissue would be recently removed from a subject without any preservation steps between the excision and the methods of the current invention. The tissue may also have been preserved by such standard tissue preparation techniques including, but not limited to, freezing, quick freezing, paraffin embedding and tissue fixation, prior to application of the methods of the current invention. Furthermore, the tissue may also be a xenograft or a syngraft on or in another host animal.

The types of agents or compounds which can be envisioned are limited only by their ability to modulate the growth of Helicobacter. The agents of the present invention may be identified and/or prepared according to any of the methods and techniques known to those skilled in the art. Preferably, the agents of the present invention are selected and screened at random or rationally selected or designed using chemical modeling techniques, based on structure-activity relationships (SAR).

For random screening, candidate agents are selected at random and assayed for their ability to modulate the growth of Helicobacter. Any of the suitable methods and techniques known to those skilled in the art may be employed to assay candidate agents.

For rational selection or design, the agent is selected based on the chemical structure of known modulators of the growth of Helicobacter. Any of the suitable methods and techniques, or modifications thereof, known to those skilled in the art may be employed for rational selection or design. For example, one skilled in the art can readily adapt currently available procedures to generate peptides, pharmaceutical agents and the like capable of modulating the growth of Helicobacter.

In another embodiment, the known modulators for use in the assay of the current invention are isothiocyanate, sulforaphane, sulforaphene, erysolin, erucin, iberin, alyssin, berteroin, iberverin, cheirolin, 5-methylsulfinylpentyl isothiocyanate, 6-hexylsulfinyl isothiocyanate, 7-methylsulfinylheptyl isothiocyanate, 8-methylsulfinyloctyl isothiocyanate, 9-methylsulfinylnonyl isothiocyanate, 10-methylsulfinyldecyl isothiocyanate, phenylethyl isothiocyanate, 4-(α-L-rhamnopyranosyloxy) benzyl isothiocyanate, 3-(α-L-rhamnopyranosyloxy)benzyl isothiocyanate, 2-(α-L-rhamnopyranosyloxy)benzyl isothiocyanate, 4-(4'-O-acetyl-α-L-rhamnopyranosyloxy) benzyl isothiocyanate or a derivative thereof. The isothiocyanates, glucosinolates or derivatives thereof for use in the methods of identifying modulators of Helicobacter growth have been described previously herein. In still another embodiment, the known modulator is sulforaphane.

The following Examples serve only to illustrate the invention, and should not be construed, in any way, to limit the invention.

EXAMPLES

Example 1

A preparation of broccoli sprout extract was delivered to H. pylori growth medium both with and without fetal calf serum (FCS) which is reported to ameliorate the effects of some antibiotics against H. pylori. The first column below indicates the dilution of broccoli sprout extract used, the second column indicates the actual sulforaphane concentration in test article.

| Test Article | | Sulforaphane effects on H. pylori strain 26695 growth | |
|---|---|---|---|
| Dilution (1/x) | Sulforaphane Conc. | Test Medium (Serum-Free) | Test Medium (+1% FCS) |
| 100 | 1940 μM | Complete inhibition | complete inhibition |
| 500 | 388 μM | Complete inhibition | complete inhibition |
| 2,500 | 78 μM | complete inhibition | complete inhibition |
| 12,500 | 16 μM | complete inhibition | >4 log reduction |
| 62,500 | 3.1 μM | slight suppression | >1 log reduction |

(3.2 μM ≈ 0.57 ppm sulforaphane)

Example 2

To assess the ability of sulforaphane to inhibit the growth of H. pylori, compared to traditional antibiotic therapies, several strains of H. pylori were cultured in the presence or absence of sulforaphane or antibiotics, and the minimum inhibitory concentrations (MIC) of each were compared. The antibiotics against which sulforaphane was compared were amoxycillin, clarithromycin and metronidazole. The data below demonstrate that sulforaphane is as effective, if not more effective, as traditional antibiotics in inhibiting the growth of H. pylori.

TABLE 1

Bacteriostatic activity of sulforaphane against amoxicillin/clarithromycin/metronidazole - susceptible strains of Helicobacter pylori (n = 32)

| | MIC (μg/ml) of | | | |
|---|---|---|---|---|
| Strain no | Amoxicillin | Clarithromycin | Metronidazole | Sulforaphane |
| 1 | 0.06 | 0.06 | 1 | 2 |
| 2 | 0.06 | 0.125 | 1 | 4 |
| 3 | 0.06 | 0.125 | 1 | 2 |
| 4 | 0.06 | 0.06 | 1 | 4 |
| 5 | 0.06 | 0.06 | 4 | 4 |
| 6 | 0.06 | 0.06 | 0.06 | 0.06 |
| 7 | 0.06 | 0.06 | 0.06 | 0.06 |
| 8 | 0.06 | 0.06 | 0.5 | 0.5 |
| 9 | 0.125 | 0.06 | 1 | 2 |
| 10 | 0.06 | 0.06 | 0.5 | 0.06 |
| 11 | 0.06 | 0.06 | 0.25 | 2 |
| 12 | 0.06 | 0.06 | 1 | 4 |
| 13 | 0.06 | 0.06 | 1 | 4 |
| 14 | 0.06 | 0.06 | 0.06 | 0.06 |
| 15 | 0.06 | 0.06 | 0.06 | 0.06 |
| 16 | 0.06 | 0.06 | 0.5 | 1 |
| 17 | 0.06 | 0.06 | 1 | 0.5 |
| 18 | 0.06 | 0.06 | 1 | 0.5 |
| 19 | 0.06 | 0.06 | 0.125 | 2 |
| 20 | 0.06 | 0.06 | 0.125 | 0.5 |
| 21 | 0.125 | 0.06 | 0.125 | 0.5 |
| 22 | 0.06 | 2 | 0.125 | 0.06 |
| 23 | 0.06 | 0.06 | 0.06 | 0.06 |
| 24 | 0.06 | 0.06 | 0.5 | 1 |
| 25 | 0.06 | 0.06 | 1 | 0.5 |
| 26 | 0.06 | 0.06 | 1 | 0.5 |
| 27 | 0.06 | 0.06 | 0.06 | 0.06 |
| 28 | 0.06 | 0.125 | 0.5 | 0.5 |
| 29 | 0.125 | 0.06 | 1 | 2 |
| 30 | 0.06 | 0.06 | 0.5 | 0.06 |

TABLE 1-continued

Bacteriostatic activity of sulforaphane against
amoxicillin/clarithromycin/metronidazole - susceptible strains of
Helicobacter pylori (n = 32)

| | MIC (μg/ml) of | | | |
|---|---|---|---|---|
| Strain no | Amoxicillin | Clarithromycin | Metronidazole | Sulforaphane |
| 31 | 0.06 | 0.06 | 0.25 | 4 |
| 32 | 0.06 | 0.06 | 1 | 2 |

TABLE 2

Bacteriostatic activity of sulforaphane against clarithromycin and/or
metronidazole - intermediate or resistant strains of Helicobacter pylori
(n = 15)

| | MIC (μg/ml) of | | | |
|---|---|---|---|---|
| Strain no | Amoxicillin | Clarithromycin | Metronidazole | Sulforaphane |
| 33 | 0.06 | 0.06 | 32 | 4 |
| 34 | 0.125 | 0.125 | 256 | 0.5 |
| 35 | 0.06 | 0.06 | 64 | 4 |
| 36 | 0.06 | 0.06 | 64 | 4 |
| 37 | 0.06 | 0.06 | 64 | 0.5 |
| 38 | 0.125 | 0.5 | 64 | 2 |
| 39 | 0.06 | 0.125 | 256 | 0.5 |
| 40 | 0.06 | 0.06 | 64 | 4 |
| 41 | 0.06 | 4 | 16 | 0.125 |
| 42 | 0.06 | 16 | 1 | 4 |
| 43 | 0.06 | 16 | 1 | 8 |
| 44 | 0.06 | 16 | 0.5 | 0.5 |
| 45 | 0.06 | 8 | 2 | 1 |
| 46 | 0.06 | 16 | 32 | 2 |
| 47 | 0.06 | 16 | 64 | 4 |

TABLE 3

Time course for Efficacy of Sulforaphane activity against
Helicobacter pylori

| | Time (h) at which 99.9% intracellular killing was observed for | | | |
|---|---|---|---|---|
| Conc. of sulforaphane Tested | HP 1* (MIC = 2 μg/ml) | HP 2*[a] (MIC = 2 μg/ml) | HP 3* (MIC = 4 μg/ml) | HP 4** (MIC = 0.06 μg/ml) |
| 1 × MIC | 8 | — | 4 | 8 |
| 5 × MIC | 8 | — | 4 | 8 |
| 10 × MIC | 8 | — | 4 | 8 |
| 20 × MIC | 8 | — | 2 | 4 |

*tested in triplicate
**tested in duplicate - definitive results will be available next week
[a]A less than 10,000-fold (99.9%) reduction in colony forming units (CFU) was observed with this strain.

Actual reductions ($\log_{10}$CFU) for this strain follow:

| Time (h) | 1x MIC | 5x MIC | 10x MIC | 20x MIC |
|---|---|---|---|---|
| 2 | 0 | 0 | 0 | −0.12 |
| 4 | −0.79 | −0.90 | −1.17 | −1.30 |
| 8 | −0.90 | −0.90 | −1.30 | −1.40 |
| 24 | −1.18 | −1.20 | −1.34 | −1.40 |
| 48 | −1.20 | −1.20 | −1.40 | −1.40 |

Example 3

Bacteria are grown in broth cultures to log phase, collected by centrifugation and resuspended in PBS. Groups of animals (mice and gerbils) are dosed with $10^9$ CFU/ml of *H. pylori* in PBS, either by gavage (100 μL delivered via a round-end cannula, or by oral inoculation (delivery of 30–50 μL of *H. pylori* in PBS via micropipet following the removal of access to food and water for 3 to 6 hours). Animal groups are housed in microisolator cages and handled by personnel wearing protective clothing. At various time-points, animals are anesthetized with metaphane, exsanguinated by cardiac puncture, and then sacrificed by cervical dislocation to assess infection status. Infection status are measured by direct culture, histology, and a rapid urease test that is highly indicative of *H. pylori* presence (Y. Tokunaga et al, *J Gastroenterol Hepatol* 15:617–621 (2000)). *H. pylori* is cultured from gastric mucosa on semi-solid culture medium with antibiotics to inhibit the growth of contaminating organisms, and colony confirmation is made based on colony morphology and microscopic examination. A pathologist examines tissues for macroscopic signs of inflammation and/or erosion, and microscopic analysis of fixed tissues is performed on paraffin sections stained by the modified Giemsa or modified Steiner method and graded on a 0–4 scale (R K Vartanian et al., *Mod Pathol*, (1998), 11:72–78; O Rotimi et al., *J Clin Pathol*, 53:756–759 (2000)). These widely used methods are initially used to optimize infection techniques, and to determine which of the *H. pylori* strains will best colonize the animals to be used in subsequent experiments. Successfully infected animals are then dosed by oral gavage or as a provision of the test compound in diets with sulforaphane or another compound as provided herein. To validate dosage, blood obtained by cardiac puncture is processed for quantitative determination of isothiocyanates and their dithiocarbamate metabolites in the serum or plasma of a subset of animals (Ye et al., *Clin Chem Acta* (2001) [in press]). Degree of inflammation is assessed with the assistance of a pathologist and a physician who are familiar with the appearance of gastric inflammation and grade such gastritis using a modified Sydney system (C S Goodwin, *J Gastroenterol Hepatol*, 6:235–237 (1991); X Y Chen et al., *J Clin Pathol*, 52:612–615 (1993)) and the 0–3 scale described by Lee et al., *Zentalbl Bakteriol*, 280:38–50 (1993), for acute inflammation, chronic inflammation and atrophy.

If in-vitro activity is identified, therapy with Moringa tree leaves or seeds, or broccoli or cauliflower sprouts or seeds, or extracts made from these items can be useful to either ameliorate or cure peptic ulcers caused by *H. pylori*. If there is anti-*H. pylori* antibiotic activity, therapy as indicated above is also effective to prevent *H. pylori* infection and theoretically reduce the incidence of stomach cancer which is related to *H. pylori* infection.

Example 4

*Helicobacter pylori* has been implicated as having a direct role in the generation of oxidative stress in colonized gastric mucosal tissue. Shirin et al. (Cancer Letters 164:127–133 (2001)) have demonstrated that *Helicobacter pylori* causes a transient initial increase (1 h) in glutathione (GSH) levels in cultured AGS cells, but that intracellular GSH stores were subsequently depleted completely after 24 h. They also showed that GSH concentrations in gastric mucosal from antral biopsies were significantly lower in *H. pylori* colonized human subjects (n=19) than in normal controls (n=38).

AGS cells are cultured in microtiter well plates and treated with concentrations of sulforaphane (SF) and 4-(α-

L-rhamnopyranosyloxy)benzyl isothiocyanate (4RBITC) designed to induce QR levels several-fold above those of untreated controls, at 48 h. Low levels of bacteria *H. pylori* (Hp) are introduced to the plates at 1, 4, and 20 h post-induction. Quinone reductase (QR; a key Phase 2 detoxification and antioxidant enzyme) levels are assessed at both one and two days after induction. Cellular GSH and protein levels are determined at these time points.

| Plate | Inducer (@24 h) | Hp Trtmnts (3/plate)* | Endpoint (QRIP, GSH, Protein) |
|---|---|---|---|
| 1 | untreated cntrl | 25 h | 48 h |
| 2 | untreated cntrl | 28 h | 48 h |
| 3 | untreated cntrl | 44 h | 48 h |
| 4 | untreated cntrl | 25 h | 72 h |
| 5 | untreated cntrl | 28 h | 72 h |
| 6 | untreated cntrl | 44 h | 72 h |
| 7 | SF (~20 uM) | 25 h | 48 h |
| 8 | SF (~20 uM) | 28 h | 48 h |
| 9 | SF (~20 uM) | 44 h | 48 h |
| 10 | SF (~20 uM) | 25 h | 72 h |
| 11 | SF (~20 uM) | 28 h | 72 h |
| 12 | SF (~20 uM) | 44 h | 72 h |
| 13 | 4RBITC (~20 uM) | 25 h | 48 h |
| 14 | 4RBITC (~20 uM) | 28 h | 48 h |
| 15 | 4RBITC (~20 uM) | 44 h | 48 h |
| 16 | 4RBITC (~20 uM) | 25 h | 72 h |
| 17 | 4RBITC (~20 uM) | 28 h | 72 h |
| 18 | 4RBITC (~20 uM) | 44 h | 72 h |

*1-fresh medium;
2-fresh medium + *H. pylori*;
3-fresh medium + heat-killed *H. pylori*

Example 5

An animal model of *H. pylori* infection is used to assess the efficacy of glucosinolates, isothiocyanates, including sulforaphane, or derivatives thereof to inhibit the growth of *H. pylori* in an in vivo setting. The animal model is described in Lozniewski et al., Infect Immun. 67(4): 1798–1805 (1999), which is hereby incorporated by reference in its entirety. Briefly, human embryonic stomachs are obtained after legal abortion and grafted onto nude (or severe combined immunodeficient) mice, under the skin of the abdomen. Eight days after implantation, the abdominal skin is reopened and gastric juice from the fetal stomachs is aspirated, to check the acidity, and a catheter is implanted into the grafted stomach. Subsequent to catheter implantation, *H. pylori* is introduced into the grafted stomach, via the catheter, and allowed to infect the tissue. At various time points after the initial *H. pylori* inoculation, the infection is evaluated by testing the acidity of the gastric juice and by histological evaluation of biopsies.

After successful infections are confirmed, the stomachs are dosed with, for example, sulforaphane, through the catheter and infections are re-evaluated at various time points to determine the efficacy of sulforaphane in treating *H. pylori* infections.

What is claimed is:

1. A method of treating a subject having a Helicobacter infection comprising administering an antibacterially effective amount of a composition to said subject, said composition consisting essentially of one or more of a glucosinolate, an isothiocyanate, a derivative of a glucosinolate, or a derivative of an isothiocyanate.

2. The method of claim 1, wherein said isothiocyanate is one or more of sulforaphane, sulforaphene, erysolin, erucin, iberin, alyssin, berteroin, iberverin, cheirolin, 5-methylsulfinylpentyl isothiocyanate, 6-methylsulfinylhexyl isothiocyanate, 7-methylsulfinylheptyl isothiocyanate, 8-methylsulfinyloctyl isothiocyanate, 9-methylsulfinylnonyl isothiocyanate, 10-methylsulfinyldecyl isothiocyanate, phenylethyl isothiocyanate, 4-(α-L-rhamnopyranosyloxy)benzyl isothiocyanate, 3-(α-L-rhamnopyranosyloxy)benzyl isothiocyanate, 2-(α-L-rhamnopyranosyloxy)benzyl isothiocyanate, 4-(4'-O-acetyl-α-L-rhamnopyranosyloxy)benzyl isothiocyanate or a derivative thereof.

3. The method of claim 2, wherein said isothiocyanate is sulforaphane.

4. The method of claim 1, wherein said composition is a food supplement, a dietary supplement or a food additive.

5. The method of claim 4, wherein said composition consists essentially of a glucosinolate or a derivative thereof.

6. The method of claim 1, wherein said composition is a pharmaceutical composition.

7. The method of claim 6, wherein said pharmaceutical composition is administered orally.

8. The method of claim 1, wherein said subject having a Helicobacter infection is suffering from an ulcer.

9. The method of claim 1, wherein said subject is suffering from, or at risk for developing stomach cancer.

10. The method of claim 1, wherein said Helicobacter is *Helicobacter pylori*.

11. The method of claim 1, further comprising administering an antibiotic to said subject.

12. The method of claim 11, wherein said antibiotic is selected from the group consisting of one or more of amoxycillin and clarithromycin.

13. A method for inhibiting the growth of Helicobacter, comprising administering to said Helicobacter an antibacterially effective amount of an agent, said agent consisting essentially of one or more of a glucosinolate, an isothiocyanate, a derivative of a glucosinolate, or a derivative of an isothiocyanate.

14. The method of claim 13, wherein said isothiocyanate is one or more of sulforaphane, sulforaphene, erysolin, erucin, iberin, alyssin, berteroin, iberverin, cheirolin, 5-methylsulfinylpentyl isothiocyanate, 6-methylsulfinylhexyl isothiocyanate, 7-methylsulfinylheptyl isothiocyanate, 8-methylsulfinyloctyl isothiocyanate, 9-methylsulfinylnonyl isothiocyanate, 10-methylsulfinyldecyl isothiocyanate, phenylethyl isothiocyanate, 4-(α-L-rhamnopyranosyloxy)benzyl isothiocyanate, 3-(α-L-rhamnopyranosyloxy)benzyl isothiocyanate, 2-(α-L-rhamnopyranosyloxy)benzyl isothiocyanate, 4-(4'-O-acetyl-α-L-rhamnopyranosyloxy)benzyl isothiocyanate or a derivative thereof.

15. The method of claim 13, wherein said isothiocyanate is sulforaphane.

16. The method of claim 13, wherein said Helicobacter is *Helicobacter pylori*.

17. The method of claim 13, wherein said agent is administered as a composition.

18. The method of claim 17, wherein said composition is a food supplement, a dietary supplement or a food additive.

19. The method of claim 18, wherein said composition consists essentially of a glucosinolate or a derivative thereof.

20. The method of claim 17, wherein said composition is a pharmaceutical composition.

21. The method of claim 13, further comprising administering an antibiotic to said Helicobacter.

22. The method of claim 21, wherein said antibiotic is selected from the group consisting of one or more of amoxycillin and clarithromycin.

23. The method of claim 1, wherein the composition consists essentially of a combination of one or more glucosinolates, isothiocyanates, derivatives of glucosinolates, and/or derivatives of isothiocyanates.

24. The method of claim 1, further comprising administering an $H_2$ inhibitor to said subject.

25. The method of claim 24, wherein said $H_2$ inhibitor is omeprazol.

26. The method of claim 13, wherein the agent consists essentially of a combination of one or more glucosinolates, isothiocyanates, derivatives of glucosinolates, and/or derivatives of isothiocyanates.

27. The method of claim 13, further comprising administering an $H_2$ inhibitor to said Helicobacter.

28. The method of claim 27, wherein said $H_2$ inhibitor is omeprazol.

29. A method of treating a subject having a Helicobacter infection, comprising administering an antibacterially effective amount of a pharmaceutical composition to said subject, said pharmaceutical composition comprising one or more isothiocyanates selected from the group consisting of sulforaphane, sulforaphene, erysolin, erucin, iberin, alyssin, berteroin, iberverin, cheirolin, 5-methylsulfinylpentyl isothiocyanate, 6-methylsulfinylhexyl isothiocyanate, 7-methylsulfinylheptyl isothiocyanate, 8-methylsulfinyloctyl isothiocyanate, 9-methylsulfinylnonyl isothiocyanate, 10-methylsulfinyldecyl isothiocyanate, phenylethyl isothiocyanate, 4-(α-L-rhamnopyranosyloxy)benzyl isothiocyanate, 3-(α-L-rhamnopyranosyloxy)benzyl isothiocyanate, 2-(α-L-rhamnopyranosyloxy)benzyl isothiocyanate, 4-(4'-O-acetyl-α-L-rhamnopyranosyloxy) benzyl isothiocyanate, or a derivative thereof.

30. The method of claim 29, wherein said isothiocyanate is sulforaphane.

31. The method of claim 29, wherein said pharmaceutical composition is administered orally.

32. The method of claim 29, wherein said subject having a Helicobacter infection is suffering from an ulcer.

33. The method of claim 29, wherein said subject is suffering from, or at risk for developing, stomach cancer.

34. The method of claim 29, wherein said Helicobacter is *Helicobacter pylori*.

35. The method of claim 29, wherein the composition comprises a combination of two or more of said isothiocyanates or derivatives thereof.

36. The method of claim 29, further comprising administering an antibiotic to said subject.

37. The method of claim 36, wherein said antibiotic is selected from the group consisting of one or more of amoxycillin and clarithromycin.

38. The method of claim 29, further comprising administering an $H_2$ inhibitor to said subject.

39. The method of claim 38, wherein said $H_2$ inhibitor is omeprazol.

40. A method of inhibiting the growth of Helicobacter comprising administering to said Helicobacter an antibacterially effective amount of a pharmaceutical composition, said pharmaceutical composition comprising one or more isothiocyanates selected from the group consisting of sulforaphane, sulforaphene, erysolin, erucin, iberin, alyssin, berteroin, iberverin, cheirolin, 5-methylsulfinylpentyl isothiocyanate, 6-methylsulfinylhexyl isothiocyanate, 7-methylsulfinylheptyl isothiocyanate, 8-methylsulfinyloctyl isothiocyanate, 9-methylsulfinylnonyl isothiocyanate, 10-methylsulfinyldecyl isothiocyanate, phenylethyl isothiocyanate, 4-(α-L-rhamnopyranosyloxy) benzyl isothiocyanate, 3-(α-L-rhamnopyranosyloxy)benzyl isothiocyanate, 2-(α-L-rhamnopyranosyloxy)benzyl isothiocyanate, 4-(4'-O-acetyl-α-L-rhamnopyranosyloxy) benzyl isothiocyanate, or a derivative thereof.

41. The method of claim 40, wherein said isothiocyanate is sulforaphane.

42. The method of claim 40, wherein said Helicobacter is *Helicobacter pylori*.

43. The method of claim 40, wherein the composition comprises a combination of two or more of said isothiocyanates or derivatives thereof.

44. The method of claim 40, further comprising administering an antibiotic to said Helicobacter.

45. The method of claim 44, wherein said antibiotic is selected from the group consisting of one or more of amoxycillin and clarithromycin.

46. The method of claim 40, further comprising administering an $H_2$ inhibitor to said subject.

47. The method of claim 46, wherein said $H_2$ inhibitor is omeprazol.

48. The method of claim 1, wherein said subject is a human.

49. The method of claim 1, wherein said subject is non-human animal.

50. The method of claim 1, wherein said subject is a non-human mammal.

51. The method of claim 1, wherein said subject is a non-human primate.

\* \* \* \* \*